(12) United States Patent
Crosby et al.

(10) Patent No.: US 10,595,760 B2
(45) Date of Patent: Mar. 24, 2020

(54) COMPLIANT SYRINGE SYSTEM, A METHOD OF MAKING, AND OF USING THE SAME

(71) Applicant: University of Massachusetts, Boston, MA (US)

(72) Inventors: Alfred J. Crosby, Amherst, MA (US); Shruti Rattan, Amherst, MA (US)

(73) Assignee: UNIVERSITY OF MASSACHUSETTS, Boston, MA (US)

(*) Notice: Subject to any disclaimer, the term of this patent is extended or adjusted under 35 U.S.C. 154(b) by 451 days.

(21) Appl. No.: 15/146,919

(22) Filed: May 5, 2016

(65) Prior Publication Data

US 2016/0324455 A1 Nov. 10, 2016

Related U.S. Application Data

(60) Provisional application No. 62/156,951, filed on May 5, 2015.

(51) Int. Cl.
*A61B 5/15* (2006.01)
*A61M 5/42* (2006.01)
(Continued)

(52) U.S. Cl.
CPC .... *A61B 5/150152* (2013.01); *A61B 5/15003* (2013.01); *A61B 5/153* (2013.01);
(Continued)

(58) Field of Classification Search
CPC ...... A61M 5/32; A61M 5/329; A61M 5/3293; A61M 5/422; A61M 5/315; A61M 5/3286;
(Continued)

(56) References Cited

U.S. PATENT DOCUMENTS 5,267,961 A * 12/1993 Shaw ................. A61M 5/3234
604/110
5,313,969 A * 5/1994 Hsieh ................. A61B 5/15003
141/65
(Continued)

FOREIGN PATENT DOCUMENTS

JP 2001212231 A 8/2001
JP 2005087520 A 4/2005

OTHER PUBLICATIONS

Egekvist et al.; "Pain and mechanical injury of human skin following needle insertions"; European Journal of Pain; 1993; 3; pp. 41-49.
(Continued)

*Primary Examiner* — Brandy S Lee
(74) *Attorney, Agent, or Firm* — Cantor Colburn LLP (57) ABSTRACT

In an embodiment, a syringe needle comprises a helical portion located in between a needle tip portion and a distal portion. In another embodiment, a compliant article comprises a casing tube comprising a tube end opening located at a needle tube end of the casing tube, a distal tube opening located at a distal tube end of the casing tube, and an inner tube space; and a syringe needle that traverses the tube end opening; wherein the compliant article comprises a compliant portion that allows for a reduced insertion pressure of the syringe needle as compared to an insertion pressure of a corresponding syringe needle in an article without the compliant portion.

17 Claims, 4 Drawing Sheets

(51) Int. Cl.
*A61B 5/153* (2006.01)
*A61M 5/32* (2006.01)
*A61B 5/151* (2006.01)

(52) U.S. Cl.
CPC .... *A61B 5/15016* (2013.01); *A61B 5/150022* (2013.01); *A61B 5/15142* (2013.01); *A61B 5/150236* (2013.01); *A61B 5/150244* (2013.01); *A61B 5/150389* (2013.01); *A61B 5/150511* (2013.01); *A61B 5/150526* (2013.01); *A61B 5/150732* (2013.01); *A61M 5/32* (2013.01); *A61M 5/329* (2013.01); *A61M 5/422* (2013.01); *A61M 5/3293* (2013.01)

(58) Field of Classification Search
CPC .............. A61M 5/347; A61B 5/150389; A61B 5/150511; A61B 5/150526; A61B 5/150152; A61B 5/150236; A61B 5/150732; A61B 5/150022; A61B 5/15003; A61B 5/15016; A61B 5/150244; A61B 5/153; A61B 5/15142
See application file for complete search history.

(56) References Cited

U.S. PATENT DOCUMENTS

| | | | | |
|---|---|---|---|---|
| 6,235,003 | B1* | 5/2001 | Dysarz | A61M 5/3232 604/110 |
| 6,605,067 | B1* | 8/2003 | Larsen | A61M 5/3287 604/192 |
| 6,770,051 | B2* | 8/2004 | Hughes | A61M 5/007 600/420 |
| 7,740,600 | B2 | 6/2010 | Slatkine et al. | |
| 2001/0051831 | A1* | 12/2001 | Subba Rao | A61F 2/3609 623/22.42 |
| 2003/0236497 | A1* | 12/2003 | Fremming | B01L 3/502 604/126 |
| 2005/0171485 | A1* | 8/2005 | Larsen | A61M 5/326 604/198 |
| 2008/0215039 | A1 | 9/2008 | Slatkine et al. | |

OTHER PUBLICATIONS

Egekvist et al.; "Regional variations in pain to controlled mechanical skin traumas from automatic needle insertions and relations to ultrasonography"; Skin Res. and Tech.; 1995; 5; pp. 247-254; ISSN 0909-752X.

Fakhouri et al. "Puncture mechanics of soft solids"; Royal Society of Chemistry; Soft Matter 2015, 11; pp. 4723-4730.

Gill et al.; "Does Needle Size Matter?"; Journal of Diabetes Science and Technology; vol. 1; Issue 5; Sep. 2007; pp. 725-729.

Hamilton; "Needle Phobia: A Neglected Diagnosis"; Journal of Famil Practice; Aug. 1995; V41, N2; 13 pages; ISSN: 0094-3509.

Hoskins; "The Genteel Poker: A Next Gen of Pain-Free Lancing Device?"; http://www.healthline.com/diabetesmine/the-genteel-poker-a-next-gen-of-pain-free-lancing-device; Published Mar. 5, 2014; 5 pages.

Laurent "Evaluation of the clinical performance of a new intradermal vaccine administration technique and associated delivery system"; Science Direct; VAccine 25; 2007; pp. 8833-8842.

Mitragotri; "Current status and future prospects of needle-free liquid jet injectors"; Nature Reviews; Drug Discovery; vol. 5; Jul. 2006; pp. 543-548.

Ngoma et al. "Barriers and motivators to blood donation among university students in Japan: development of a measurement tool"; VoxSanguinis; 105; 2013; pp. 219-224.

Oka et al.; "Fabrication of a micro needle for a trace blood test"; Sensors and Actuators A; 97-98; 2002; pp. 478-485.

Park et al.; "Er:YAG laser pulse for small-dose splashback-free microjet transdermal drug delivery"; Optics Letters; vol. 37; No. 18; Sep. 15, 2012; pp. 3894-3896.

Sullivan et al.; "Dissolving Polymer Microneedle Patches for Influenza Vaccination"; Nat. Med.; 16(8); Aug. 2010; 5 pages.

Taddio et al.; "Survey of the prevalence of immunization non-compliance due to needle fears in children and adults"; Vaccine 30; 2012; pp. 4807-4812.

* cited by examiner

COMPLIANT SYRINGE SYSTEM, A METHOD OF MAKING, AND OF USING THE SAME

CROSS-REFERENCE TO RELATED APPLICATION

This application claims the benefit of U.S. Provisional Patent Application Ser. No. 62/156,951 filed May 5, 2015. The related application is incorporated herein in its entirety by reference.

GOVERNMENT FUNDING

This invention was made with government support under award number 1304724 awarded by the National Science Foundation Division of Materials Research. The government has certain rights in the invention.

BACKGROUND

Hypodermic needle insertion is a critical aspect of several invasive medical procedures such as immunization, percutaneous drug delivery, biopsy, and diabetes lancing. However, in spite of being a routine medical procedure, statistics show that a large and growing number of people are suffering from needle phobia. Needle phobia, also known as Trypanophobia, is a morbid fear of medical procedures involving hypodermic needles or injections that has been on a steady rise amongst adults and children. *The Journal of family practice*, 41(2):169-75, August 1995 reported that, in 1995, needle phobia affected 10% of the participating population. However, a survey in *Vaccine*, 30(32):4807-12, Jul. 2012, involving around 2,000 people reported that 24% of adults and 63% of children had a fear of needles and that non-compliance with immunization due to needle fear was reported in 7% and 8% of parents and children, respectively. A similar survey reported in *Vox sanguinis*, 105(3):219-24, October 2013, showed that close to 42.8% of students will not donate blood due to fear, including a fear of needles.

Medical practitioners have adopted several remedies for reducing the pain associated with needle insertion such as applying pressure on or pinching up the skin of the target area, skillful positioning of the needle, and changing the posture of the individual prior to insertion. However, these approaches are not reliable as they depend upon the dexterity of the practitioner.

An improved needle insertion system with reduced pain associated with insertion is therefore desired. It would further be advantageous if the needle could be easily adapted to standard syringes typically used by medical practitioners, could be injected into various injection sites (such as dermal, subcutaneous, or muscular tissues), and/or could be tailored to a patient's pain sensitivity.

BRIEF SUMMARY

Disclosed herein is a compliant syringe system, a method of making, and of using the same.

In an embodiment, a syringe needle comprises a helical portion located in between a needle tip portion and a distal portion.

In an embodiment, a compliant article comprises a casing tube comprising a tube end opening located at a needle tube end of the casing tube, a distal tube opening located at a distal tube end of the casing tube, and an inner tube space; and a syringe needle that traverses the tube end opening; wherein the compliant article comprises a compliant portion that allows for a reduced insertion pressure of the syringe needle as compared to an insertion pressure of a corresponding syringe needle in an article without the compliant portion.

In an embodiment, a syringe casing comprises a casing tube comprising a tube end opening located at a needle tube end of the casing tube and a distal tube opening located at a distal tube end of the casing tube; wherein a straight needle traverses the tube end opening or wherein the needle tip portion of the syringe needle of any one of the preceding claims traverses the tube end opening such that the helical portion and the distal portion are located in an inner tube space of the casing tube.

In an embodiment, a syringe system comprises a syringe comprising an inner syringe space, a syringe hub located at a hub barrel end of the syringe, and a distal barrel opening located at a distal syringe end of the syringe; and a plunger located in the inner syringe space; wherein the syringe is located in an inner tube space of a syringe casing; and wherein a distal portion of a syringe needle is located in the syringe hub or a straight portion of the straight needle is located in the syringe hub.

In an embodiment, a syringe system comprises a syringe comprising an inner syringe space, a syringe hub located at a hub barrel end of the syringe, and a distal barrel opening located at a distal syringe end of the syringe; a plunger located in the inner syringe space; a straight needle; and a spring; wherein the syringe is located in an inner tube space of a syringe casing; wherein the spring is located in the inner tube space in between a tube end opening and the syringe and/or wherein the spring is located in a spring tube portion located at a distal tube end.

In an embodiment, a syringe system comprises a syringe comprising an inner syringe space, a syringe hub located at a hub barrel end of the syringe, and a distal barrel opening located at a distal syringe end of the syringe; and a plunger located in the inner syringe space; a straight needle; and a filled portion; wherein the syringe is located in an inner tube space of a syringe casing; wherein the filled portion is located in the inner tube space in between a tube end opening and the syringe and/or wherein the filled portion is located in a spring tube portion located at a distal tube end; wherein the filled portion optionally has a modulus of 1 kilopascal to 10 megapascal.

In an embodiment, a method for making a syringe system comprises inserting a syringe into an inner tube space of a casing tube.

In an embodiment, a method of ejecting a fluid from a syringe system, comprises applying a pressure to a plunger and ejecting a fluid located in an inner syringe space of a syringe through the needle.

In an embodiment, a method of withdrawing a fluid from a patient into a syringe system comprises inserting a needle tip portion or a straight needle into the patient; and withdrawing the fluid from the patient into an inner syringe space of the syringe through the needle by applying a force to a plunger.

In another embodiment, a method of ejecting or taking in a fluid using a compliant syringe system comprising: inserting a syringe needle into a patient; and applying a pressure to the fluid and ejecting the fluid located in an inner tube space through the syringe needle; or withdrawing the fluid from the patient into the inner tube space through the syringe needle; wherein the compliant syringe system comprises a casing tube comprising a tube end opening located at a needle tube end of the casing tube, a distal tube opening located at a distal tube end of the casing tube, and the inner tube space; wherein the syringe needle traverses the tube end opening; wherein the compliant syringe system comprises a compliant portion that allows for a reduced insertion pressure of the syringe needle as compared to an insertion pressure of a corresponding syringe needle in a syringe system without the compliant portion.

The above described and other features are exemplified by the following figures and detailed description.

BRIEF DESCRIPTION OF THE DRAWINGS

Refer now to the figures, which are exemplary embodiments, and wherein the like elements are numbered alike and which are presented for the purposes of illustrating the exemplary embodiments disclosed herein and not for the purposes of limiting the same.

DETAILED DESCRIPTION

Currently, there are several products available in the healthcare market for reducing the pain associated with needle insertion; however each product has distinct limitations. For example, GENTEEL™ (commercially available from Genteel, Midland, Tex.) uses the precise control of penetration depth to avoid contact with nerve endings plus vibration and vacuum to soothe the skin. This technique though can only be used for blood withdrawal and is both expensive and bulky. COMFORT-IN™ (commercially available from Eternity Healthcare, Vancouver, BC) is a needle-less injection system that delivers medication as a liquid jet stream that penetrates the skin through a micro-orifice. This needle-less injection technique has the drawback of only being applicable for use in subcutaneous injections. It further has variability in penetration depth, which depends upon the skin's mechanical properties and can lead to occasional pain. FLUZONE™ (commercially available from Sanofi Pasteur Inc.) is an intradermal vaccine that uses an ultra-fine needle with a length that is 90% shorter than typical needles and avoids contact with muscle, thus preventing muscle ache. The fine, short needle though can lead to unsteady insertion due to buckling of the needle and can limit the amount of the fluid to be injected. While these and other emerging technologies sound promising; they are often restricted to perform only one kind of operation.

It was surprisingly discovered that the critical pressure required to puncture the surface of a polymer gel (also referred to as the insertion pressure) decreases as the compliance of the needle insertion system increases. As reduced pain is associated with reduced insertion pressure, as evidenced by Eur J Pain. 1999 March; 3(1):41-49 and Skin Res Technol. 1999; 247-54, the Inventors hereof developed a compliant syringe system that overcomes the drawbacks described above for current pain-reducing syringe technologies. The compliant syringe system comprises a compliant portion that can be, for example, a helical portion of the syringe needle, a spring, a filled portion, or a combination comprising one or more of the foregoing. The compliant syringe system comprises a compliant portion that allows for a reduced insertion pressure of the syringe needle as compared to an insertion pressure of a corresponding syringe needle in a syringe system without the compliant portion. The corresponding syringe needle of the syringe system without the compliant portion can have the same inner and outer diameter as the syringe needle of the compliant syringe system.

The compliant syringe system can be easily designed to achieve a specified compliance value. For example, the compliance value can be tailored by specifying, in either or both of a helical portion of the syringe needle and the spring, one or more of the number of helical loops, a wall thickness of the helical portion, a pitch of the loops, and a loop diameter; and/or the compliance value can be tailored by specifying a stiffness of a filled portion. Accordingly, the compliant syringe system has the benefit of being easily tailored to suit a patient's pain sensitivity by selecting a needle with a desired compliance.

The compliant syringe system has the added benefit that it can be used for both injecting and withdrawing fluid; it allows access to various injection sites (such as one or more of dermal, subcutaneous, and muscular injection sites of the skin tissue), and it can be easily coupled to syringes or withdrawing tubes commonly used by medical practitioners.

The compliant syringe system can comprise a straight syringe needle or a syringe needle with a helical portion (referred to herein as a helical needle). As used herein, the needle tip portion is the portion of the needle (for example, of the straight needle or of the helical needle) that can be inserted into the patient. The tip of the needle tip portion can be beveled or it can be flat. The cross-section of the needle tip portion can be circular, ovoid, and the like. The helical needle comprises a helical portion located in between a needle tip portion and a distal portion. The helical portion comprises at least one helical loop, specifically, 1 to 200 loops, more specifically, 1 to 20 loops. The helical needle can comprise a metal (such as a flexible metal, for example, a nickel, titanium alloy), a plastic (such as a silicon polymer or a polyolefin (such as polypropylene and polyethylene)), or a combination comprising at least one of the foregoing. The distal portion (for example, of the straight needle or of the helical needle) is configured for coupling with a syringe. For example, the distal portion can be directly inserted into the syringe or the distal portion can be coupled to a needle hub.

The needle tip portion can have an outer diameter of 1.7 to 0.1 millimeters (mm) The needle tip portion can have an inner diameter of 1.3 to 0.005 mm, specifically, 1.3 to 0.05 mm. The needle tip portion can have a gauge of 16 to 35, for example, 27 to 35 gauge. The gauge of the needle, the inner diameter, and the outer diameter can be the same or different in each of the needle tip portion, the helical portion, and the distal portion. The length of the needle tip portion and the length of the distal portion can each independently be 0.3 to 50 mm, specifically, 1 to 25 mm, more specifically, 1 to 10 mm. The length of the helical needle or of the straight needle can be 5 to 150 mm, specifically, 10 to 75 mm, more specifically, 10 to 50 mm.

Figure 1:
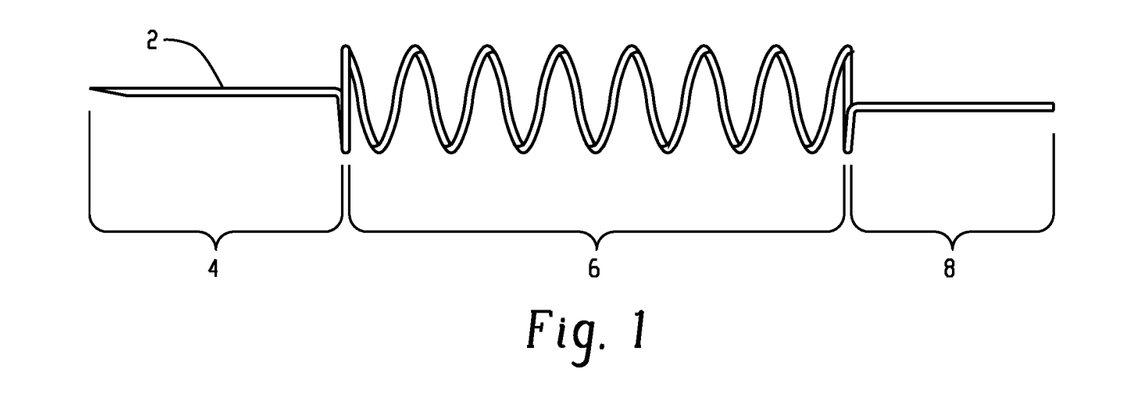
FIG. 1 is an illustration of an embodiment of a compliant needle.
Figure 2:
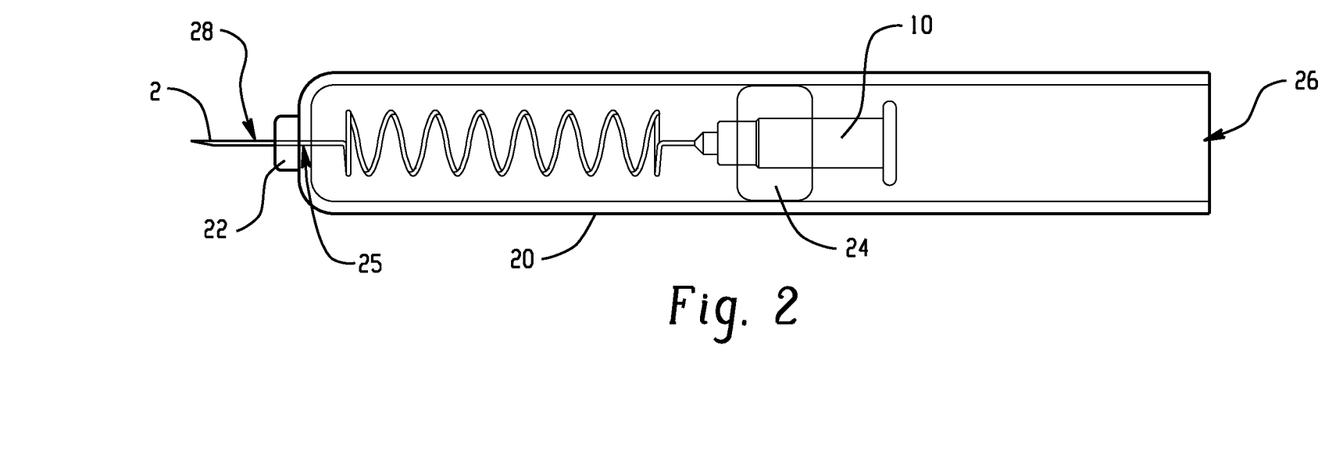
FIG. 2 is an illustration of an embodiment of a casing.

An example of helical needle 2 is illustrated in FIG. 1, where helical needle 2 comprises helical portion 6 located in between needle tip portion 4 and distal portion 8. While FIG. 1 illustrates that the needle comprises a straight distal portion, it is understood that other configurations can be considered. Distal portion 8 can comprise needle hub 10 as illustrated in FIG. 2, where a syringe can be threadably attached onto the hub or that can be slid into the hub.

The needle, for example, the needle tip portion can traverse through an opening in a casing tube. For the helical needle, the helical portion and the distal portion can be located within an inner tube space of the casing tube.

A stabilizer can be located in the casing tube to secure the distal portion of the needle from moving in the casing tube. The stabilizer can be formed as a single part when forming the casing tube or can be an insert that is separate from the casing tube. The stabilizer can comprise an opening, that one or both of the distal portion of the helical needle and a needle hub can traverse. FIG. 2 illustrates casing tube 20 with helical needle 2 located therein. Needle tip portion 4 traverses an opening in casing tube 20 and in casing hub 22. Needle hub 10 traverses an opening in stabilizer 24. Syringe casing tube 20 comprises tube end opening 25 located at a needle tube end of the casing tube and distal tube opening 26 located at a distal tube end of the casing tube.

A syringe can be inserted into the distal tube opening of the syringe casing and can be engaged with the syringe needle such that a fluid in the syringe can pass from the syringe into the helical needle when a force is applied to the plunger of the syringe. Likewise, a collection tube can be inserted into the distal tube opening of the syringe casing and can be engaged with the syringe needle such that a fluid from the patient can pass through the needle into the collection tube. Conversely, the compliant syringe system can be free of a separate syringe or the collection tube and the fluid can pass directly to or from the inner tube space through the syringe needle.

Figure 3:
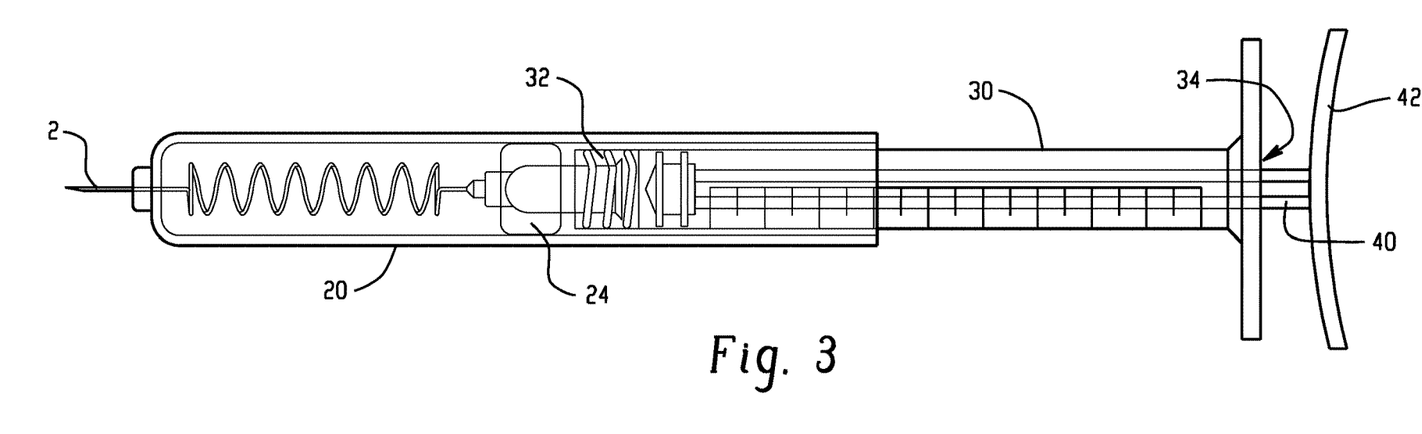
FIG. 3 is an illustration of an embodiment of a compliant syringe system comprising a syringe coupled to a compliant needle.
Figure 4:
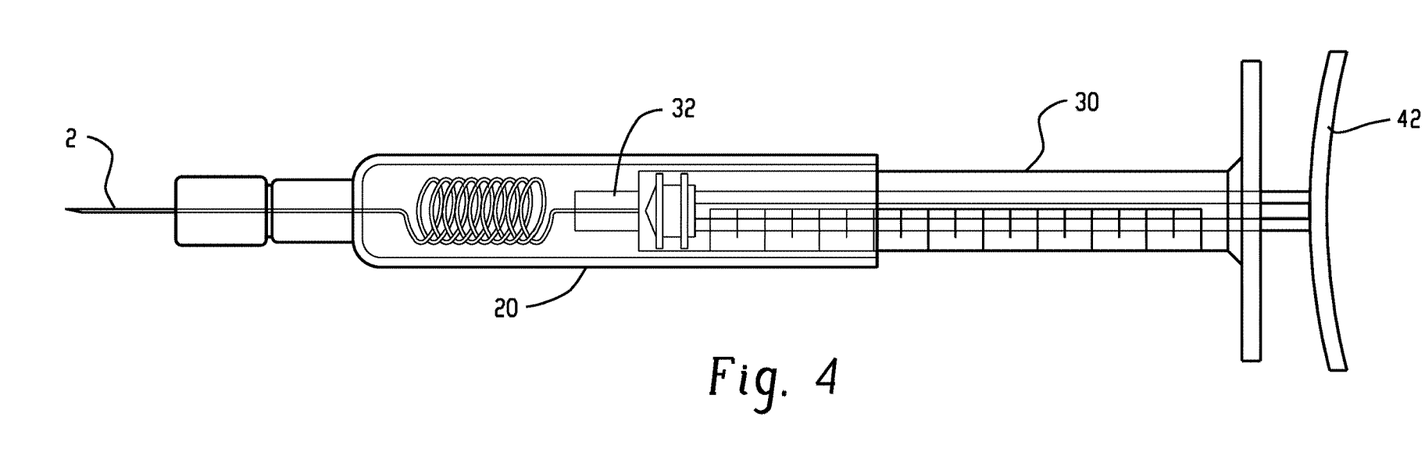
FIG. 4 is an illustration of embodiment of a compliant syringe system comprising a syringe coupled to a compliant needle.

The distal portion of the syringe needle can directly traverse through a hole in the syringe, as illustrated in FIG. 4, or a needle hub can engage with a syringe hub as illustrated in FIG. 3. For example, the needle hub can be configured for use with a LUER-LOK™ system (commercially available from Becton, Dickenson and company, Franklin Lakes, N.J.). For example, the needle hub can be threadably engaged with the syringe hub, where the needle hub can be threadably inserted into a threaded syringe hub or the syringe hub can be threadably inserted into a threaded needle hub. Conversely, the syringe hub can be a slip tip that is not threaded and that is inserted into the needle hub. The needle hub and the syringe hub can be locked together with a locking mechanism, for example, that can lock the two hubs together through the application of a force during insertion of the syringe into or onto the needle hub. For example, the needle hub can be configured for use with a SAFETY-LOK™ system (commercially available from Becton, Dickenson and Company, Franklin Lakes, N.J.). Likewise, the distal portion of the syringe needle can directly traverse through a hole in a collection tube or a needle hub can engage with a collection tube hub.

FIG. 3 and FIG. 4 illustrate embodiments of a compliant syringe system comprising helical needle 2. FIG. 3 illustrates that needle hub 10 is threadably engaged with syringe hub 32 that is illustrated as an internally threaded LUER-LOK™. FIG. 4 illustrates that the distal portion of the helical needle 2 traverses through an opening in the syringe 30. Syringe hub 32 is located on an opposite end of the syringe 30 as distal barrel opening 34. Plunger 40 comprising plunger push location 42 traverses distal barrel opening 34 and is located in an inner syringe space of the syringe.

Figure 5:
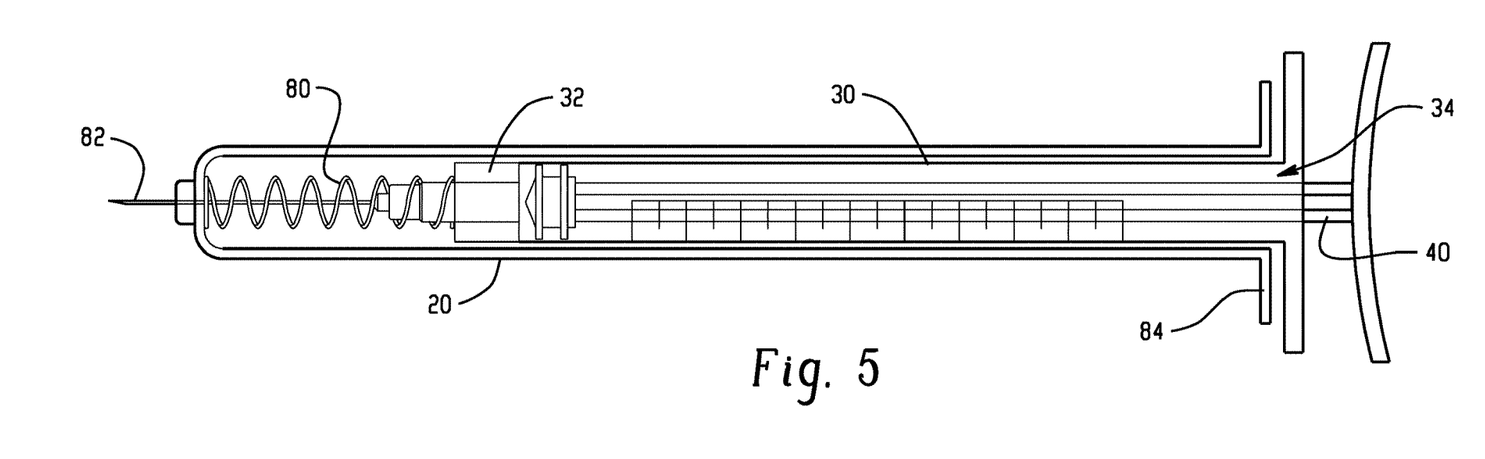
FIG. 5 is an illustration of an embodiment of a compliant syringe system comprising a spring.
Figure 6:
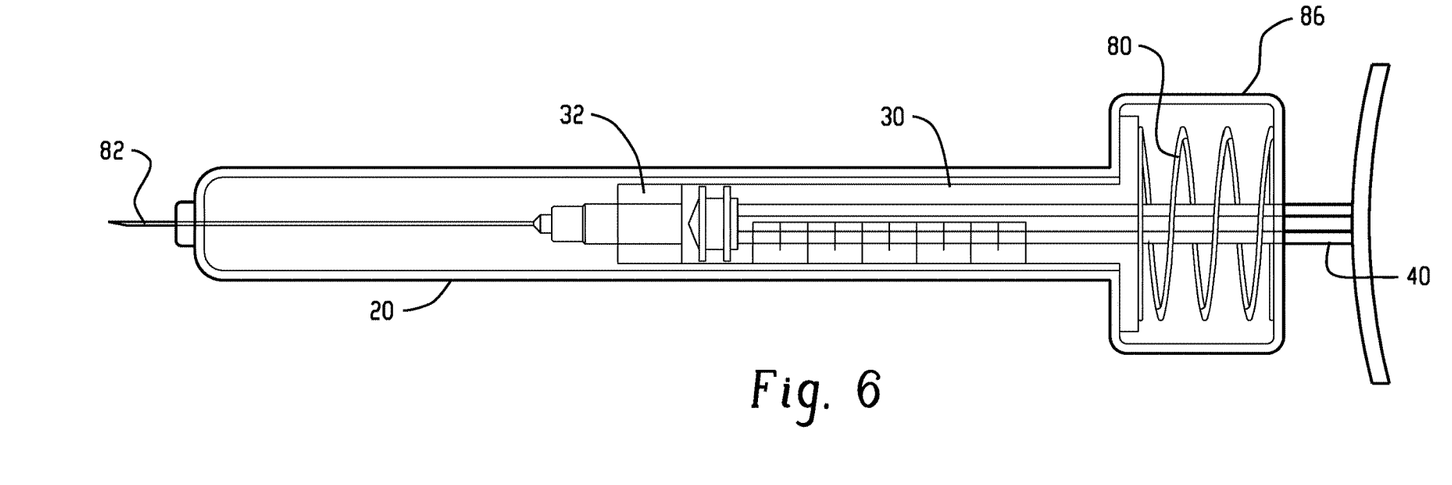
FIG. 6 is an illustration of an embodiment of a compliant syringe system comprising a spring.

FIG. 5 and FIG. 6 illustrate embodiments of a compliant syringe system comprising a straight needle and a spring. FIG. 5 illustrates that spring 80 can be located in casing tube 20 and can helically surround straight needle 82. Casing tube 20 can comprise ridge 84 that, during use, can act to stabilize syringe barrel 30 in casing tube 20. The ridge of the casing tube and a ridge of the syringe or of a collection tube can be locked together via a locking means, for example, via a clip, to stabilize the syringe barrel or the collection tube, for example, during insertion of the needle.

FIG. 6 illustrates that spring 80 can be located at the distal end of the compliant syringe system. Spring 80 can be located in spring tube portion 86 that can have a diameter greater than that of the diameter of casing tube 20. Spring tube portion 86 can have an opening such that the syringe and/or the plunger can be inserted therein.

Figure 7:
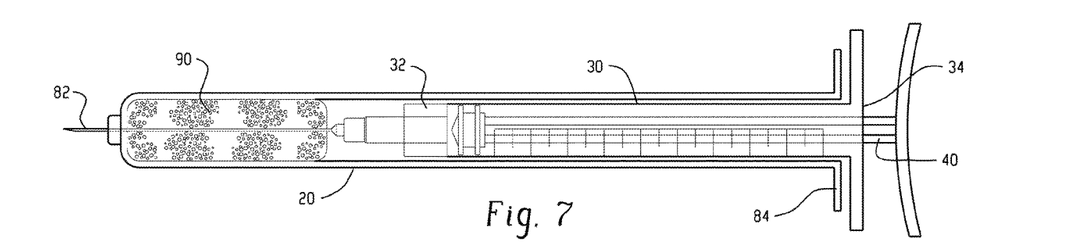
FIG. 7 is an illustration of an embodiment of a compliant syringe system comprising a filled portion.

FIG. 7 illustrates that the compliant syringe system can comprise filled portion 90. Filled portion 90 can comprise one or both of a gel (for example, a hydrogel) and a foam. Filled portion 90 can comprise an elastomer. Filled portion 90 can have a modulus, E, of 1 kilopascal (kPa) to 10 megapascal (MPa). Straight needle 82 can traverse filled portion 90 or a channel can be formed therein such that the fluid can flow from the syringe through the channel and into straight needle 82 or such that the fluid can flow from straight needle 82 through the channel to the syringe. The channel can have the same diameter as the inner diameter of the needle tip portion. The channel can have the same diameter as the outer diameter of the needle tip portion. The channel can have a varying diameter to enable coupling to an opening in the syringe and to the needle tip portion.

It is noted that while FIG. 5-7 are illustrated as employing a straight needle, that the straight needle could likewise be replaced with a helical needle.

The syringe, the syringe casing, and the plunger can each independently comprise a polymer. The polymer can comprise one or both of a thermoplastic and a thermoset. The polymer can comprise a styrene methylmethacrylate copolymer, (such as ZENITE™), a cyclic olefin copolymer of ethylene and norbornene, or a combination comprising at least one of the foregoing. The polymer can comprise natural rubber, a silicone elastomer (such as a fluorinated silicone elastomer), polyisobutylene, polybutadiene, a fluorinated polyethylene (such as polytetrafluoroethylene), polyethylene (such as high density polyethylene), a chlorinated polyethylene, polypropylene, a fluorinated polypropylene, an ethylene vinyl acetate polymer, polyvinylidene fluoride, polyisoprene, polystyrene, or a combination comprising at least one of the foregoing. The polymer can comprise polyethylene.

In practice, the syringe system can be used to eject a fluid located in the inner syringe space into a patient. For example, a method of ejecting a fluid from the syringe system can comprise inserting the needle tip portion into the patient prior to applying the pressure; and applying a pressure to a plunger and ejecting a fluid located in the inner syringe space of the syringe through the needle. The fluid can comprise a medicament. Conversely, the syringe system can be used to withdraw a fluid from a patient. For example, a method of withdrawing a fluid from a patient into the syringe system can comprise inserting the needle tip portion into the patient; and withdrawing the fluid from the patient into the inner tube space through the needle by allowing the fluid to naturally flow from the patient or by applying a force, for example, to the plunger. The fluid withdrawn can comprise a bodily fluid such as blood. In either case, the needle tip portion can be inserted into one of a dermal tissue, a subcutaneous tissue, and a muscular tissue.

The compliance of the compliant syringe system can be determined based on the individual patient. For example, prior to inserting the syringe needle, the stiffness of the patient's skin tissue can be determined and a stiffness of the compliant syringe system can be selected. For example, the compliance of the syringe system relative to the patient's skin tissue can be enough to result in a decreased insertion pressure relative to a non-compliant syringe system using a needle with the same dimensions, while allowing the needle to puncture the skin tissue. Similarly, a fear level of the patient to needles can be determined and a more compliant needle can be selected for patients with a higher fear level. The compliance of the compliant syringe system can be determined based on age and/or ethnicity as both of these factors have been shown to have an effect on the skin tissue stiffness.

The following examples are provided to illustrate the compliant syringe system. The examples are merely illustrative and are not intended to limit devices made in accordance with the disclosure to the materials, conditions, or process parameters set forth therein.

EXAMPLES

Example 1

Effect of Varying the Needle Compliance on Insertion Pressure

Figure 8:
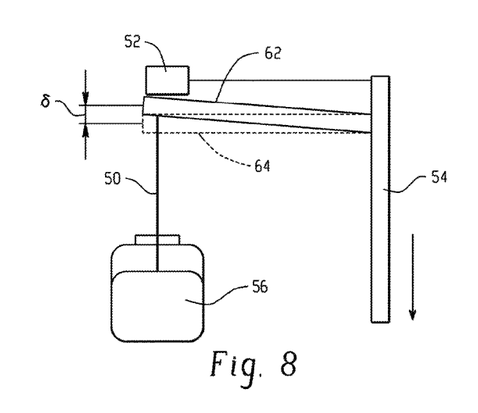
FIG. 8 is an illustration of the experimental set-up of Example 1.

In order to illustrate the effect of varying the needle compliance on the insertion pressure, a custom-built apparatus was constructed and is illustrated in FIG. 8. FIG. 8 illustrates that a cantilever, in initial cantilever position 64, is located on post 54 and that capacitance gauge 52 is located on top of the cantilever. Capacitance gauge 52 is configured to measure the deflection of the cantilever. Needle 50 is a spherically tipped needle that is located on the end of cantilever 60. The needle 50 was formed by pulling a thin glass capillary tube of diameter 0.75 mm and annealing the pulled tube to form a spherical cap with a radius of curvature, R, of 15 micrometers at the tip. A 26 gauge stainless steel flat punch needle was then inserted inside the glass capillary. Here, the cantilever is acting as the compliant portion of the syringe system and is increasing the compliance of the needle.

In the experiments, polymer gel 56 was a physically cross-linked PMMA-PnBA-PMMA triblock copolymer gel with poly(methyl methacrylate) (PMMA) end blocks and a poly(n-butyl acrylate) (PnBA) mid-block. The triblock copolymer was obtained from Kuraray Co., LTD and had end block molecular weights of 25 kilograms per mol (kg/mol) and a mid-block molecular weight of 116 kg/mol. The gel was formed by dissolving the triblock copolymer in 2-ethylhexanol (20% weight/volume) at 150° C. and then cooling to 25° C. The modulus, E, of the gel was 18 kilopascals (kPa). As the compliance of the gel is approximately equal to ½ER, the gel compliance is about 1,850 micrometers per millinewton (μm/mN).

Figure 9:
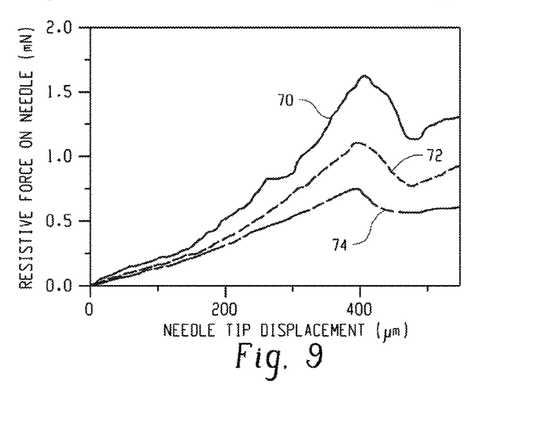
FIG. 9 is a graphical illustration of the resistive force on the needle with displacement of the needle inside a soft, polymer gel.

The gel was placed at the end of needle 50. Needle 50 was lowered to the gel at a rate of 250 micrometers per second by lowering the post 54. Upon contact with polymer gel 56, a force was exerted on needle 50 that caused deflection, δ, of the cantilever from initial cantilever position 64 to deflected cantilever position 62 as illustrated in FIG. 8. The experiment was repeated three times with varying stiffness cantilevers. The resulting resistive force on the needle in millinewtons (mN) versus displacement of needle 50 is graphically illustrated in FIG. 9, where line 70 represents the stiffest cantilever with a compliance of 1.0 μm/mN, line 72 represents the moderate cantilever with a compliance of 5.3 μm/mN, and line 74 represents the most compliant cantilever with a compliance of 58.8 μm/mN. FIG. 9 illustrates that as the needle is pressed onto the surface of the polymer gel, the resistive force increases. At a critical pressure, as illustrated by the peak in the force curves, the needle punctures the surface of the polymer gel and the force decreases with increasing displacement of the needle into the gel. FIG. 9 illustrates that the force required to puncture the polymer gel of the same stiffness and using the same needle is reduced by more than 50% merely by increasing the compliance of the needle insertion system. This decrease in force is significant and should result in a significant decrease in pain associated with needle insertion.

The above compliant syringe system is further described in the below embodiments.

In an embodiment, a compliant article comprises a casing tube comprising a tube end opening located at a needle tube end of the casing tube, a distal tube opening located at a distal tube end of the casing tube, and an inner tube space; and a syringe needle that traverses the tube end opening; wherein the compliant article comprises a compliant portion that allows for a reduced insertion pressure of the syringe needle as compared to an insertion pressure of a corresponding syringe needle in an article without the compliant portion.

In another embodiment, a method of ejecting or taking in a fluid using a compliant syringe system comprising: inserting a syringe needle into a patient; and applying a pressure to the fluid and ejecting the fluid located in an inner tube space through the syringe needle; or withdrawing the fluid from the patient into the inner tube space through the syringe needle; wherein the compliant syringe system comprises a casing tube comprising a tube end opening located at a needle tube end of the casing tube, a distal tube opening located at a distal tube end of the casing tube, and the inner tube space; wherein the syringe needle traverses the tube end opening; wherein the compliant syringe system comprises a compliant portion that allows for a reduced insertion pressure of the syringe needle as compared to an insertion pressure of a corresponding syringe needle in a syringe system without the compliant portion.

Embodiment 1

A syringe needle comprising: a helical portion located in between a needle tip portion and a distal portion.

Embodiment 2

The syringe needle of Embodiment 1, wherein a needle hub is located on the distal portion.

Embodiment 3

The syringe needle of any one of the preceding embodiments, wherein the helical portion comprises at least one helical loop or 1 to 200 helical loops.

Embodiment 4

The syringe needle of any one of the preceding embodiments, wherein the needle tip portion has an outer diameter of 1.7 to 0.1 mm.

Embodiment 5

The syringe needle of any one of the preceding embodiments, wherein the needle tip portion has an inner diameter of 1.3 to 0.005 mm, or 1.3 to 0.05 mm.

Embodiment 6

The syringe needle of any one of Embodiments 4 or 5, wherein one or both of the outer diameter and the inner diameter is constant throughout the syringe needle.

Embodiment 7

The syringe needle of any one of the preceding embodiments, wherein the length of the syringe needle is 5 to 150 mm.

Embodiment 8

The syringe needle of any one of the preceding embodiments, wherein the needle tip portion is a 16 to 35 gauge needle.

Embodiment 9

A syringe casing comprising: a casing tube comprising a tube end opening located at a needle tube end of the casing tube and a distal tube opening located at a distal tube end of the casing tube; wherein a straight needle traverses the tube end opening or wherein the needle tip portion of the syringe needle of any one of the preceding embodiments traverses the tube end opening such that the helical portion and the distal portion are located in an inner tube space of the casing tube.

Embodiment 10

The syringe casing of Embodiment 9, further comprising a stabilizer comprising a stabilizer opening, wherein one or both of the distal portion of the syringe needle and a needle hub traverses the stabilizer opening.

Embodiment 11

The syringe casing of any one of Embodiments 9-10, wherein the syringe casing comprises a ridge or a spring tube portion located at the distal tube end.

Embodiment 12

A syringe system comprising: a syringe comprising an inner syringe space, a syringe hub located at a hub barrel end of the syringe, and a distal barrel opening located at a distal syringe end of the syringe; and a plunger located in the inner syringe space; wherein the syringe is located in the inner tube space of the syringe casing of any one of Embodiments 9-11; and wherein the distal portion of the syringe needle is located in the syringe hub or a straight portion of the straight needle is located in the syringe hub.

Embodiment 13

A syringe system comprising: a syringe comprising an inner syringe space, a syringe hub located at a hub barrel end of the syringe, and a distal barrel opening located at a distal syringe end of the syringe; a plunger located in the inner syringe space; a straight needle; and a spring; wherein the syringe is located in the inner tube space of the syringe casing of any one of Embodiments 9-11; wherein the spring is located in the inner tube space in between the tube end opening and the syringe and/or wherein the spring is located in a spring tube portion located at the distal tube end.

Embodiment 14

A syringe system comprising: a syringe comprising an inner syringe space, a syringe hub located at a hub barrel end of the syringe, and a distal barrel opening located at a distal syringe end of the syringe; and a plunger located in the inner syringe space; a straight needle; and a filled portion; wherein the syringe is located in the inner tube space of the syringe casing of any one of Embodiments 9-11; wherein the filled portion is located in the inner tube space in between the tube end opening and the syringe and/or wherein the filled portion is located in a spring tube portion located at the distal tube end; wherein the filled portion optionally has a modulus of 1 kilopascal to 10 megapascal.

Embodiment 15

The syringe system of Embodiment 14, wherein the filled portion comprises a gel, a foam, or a combination comprising at least one of the foregoing and/or wherein the filled portion comprises an elastomer.

Embodiment 16

The syringe system of any one of Embodiments 12-15, wherein the distal portion or the straight needle comprises a needle hub, wherein the needle hub is threadably engaged with the syringe hub.

Embodiment 17

The syringe system of Embodiment 16, wherein the needle hub is a threaded needle hub.

Embodiment 18

The syringe system of any one of Embodiments 12-17, wherein the syringe hub is a threaded syringe hub.

Embodiment 19

The syringe system of any one of Embodiments 12-15, wherein the syringe hub is a slip tip located in the needle hub.

Embodiment 20

The syringe system of any one of Embodiments 12-15, wherein the needle hub and the syringe hub are locked together via a locking mechanism.

Embodiment 21

A method for making the syringe system of any one of Embodiments 12-20, comprising: inserting the syringe into the inner tube space of the casing tube.

Embodiment 22

The method of Embodiment 21 further comprising: inserting the needle tip portion or the straight needle into the tube end opening of the casing tube prior to inserting the syringe.

Embodiment 23

A method of ejecting a fluid from the syringe system of any one of Embodiments 12-20, comprising: applying a pressure to the plunger and ejecting a fluid located in the inner syringe space of the syringe through the needle.

Embodiment 24

The method of Embodiment 23, further comprising inserting the needle tip portion into a patient prior to applying the pressure.

Embodiment 25

The method of any one of Embodiments 23-24, wherein the fluid comprises a medicament.

Embodiment 26

A method of withdrawing a fluid from a patient into the syringe system of any one of Embodiments 14-20, comprising: inserting the needle tip portion or the straight needle into the patient; and withdrawing the fluid from the patient into the inner syringe space of the syringe through the needle by applying a force to the plunger.

Embodiment 27

The method of Embodiment 26, wherein the fluid comprises a bodily fluid.

Embodiment 28

The method of any one of Embodiments 23-27, wherein the needle tip portion is inserted into one of a dermal tissue, a subcutaneous tissue, and a muscular tissue.

Embodiment 29

The method of any one of Embodiments 23-28, further comprising determining a stiffness of the patient's epidermis and selecting a stiffness of the syringe system that is less than or equal to the stiffness of the patient's epidermis prior to the inserting.

In general, the invention can alternately comprise, consist of, or consist essentially of, any appropriate components herein disclosed. The invention can additionally, or alternatively, be formulated so as to be devoid, or substantially free, of any components, materials, ingredients, adjuvants or species used in the prior art compositions or that are otherwise not necessary to the achievement of the function and/or objectives of the present invention.

All ranges disclosed herein are inclusive of the endpoints, and the endpoints are independently combinable with each other (e.g., ranges of "up to 25 wt %, or, more specifically, 5 to 20 wt %", is inclusive of the endpoints and all intermediate values of the ranges of "5 to 25 wt %," etc.). "Combination" is inclusive of blends, mixtures, alloys, reaction products, and the like. The terms "a" and "an" and "the" herein do not denote a limitation of quantity, and are to be construed to cover both the singular and the plural, unless otherwise indicated herein or clearly contradicted by context. "Or" means "and/or." The suffix "(s)" as used herein is intended to include both the singular and the plural of the term that it modifies, thereby including one or more of that term (e.g., the film(s) includes one or more films). Reference throughout the specification to "one embodiment," "another embodiment," "an embodiment," and so forth, means that a particular element (e.g., feature, structure, and/or characteristic) described in connection with the embodiment is included in at least one embodiment described herein, and may or may not be present in other embodiments. "Optional" or "optionally" means that the subsequently described event or circumstance can or cannot occur, and that the description includes instances where the event occurs and instances where it does not. Unless defined otherwise, technical and scientific terms used herein have the same meaning as is commonly understood by one of skill in the art to which this invention belongs. Unless otherwise stated, test standards are the most recent as of the filing date of the application.

All cited patents, patent applications, and other references are incorporated herein by reference in their entirety. However, if a term in the present application contradicts or conflicts with a term in the incorporated reference, the term from the present application takes precedence over the conflicting term from the incorporated reference.

In addition, it is to be understood that the described elements can be combined in any suitable manner in the various embodiments.

While particular embodiments have been described, alternatives, modifications, variations, improvements, and substantial equivalents that are or can be presently unforeseen can arise to Applicants or others skilled in the art. Accordingly, the appended claims as filed and as they can be amended are intended to embrace all such alternatives, modifications variations, improvements, and substantial equivalents.

We claim:

1. A compliant article comprising:
   a casing tube comprising a tube end opening located at a needle tube end of the casing tube, a distal tube opening located at a distal tube end of the casing tube, and an inner tube space; and
   a syringe needle that traverses the tube end opening;
   wherein the compliant article comprises a compliant portion that allows for a reduced insertion pressure of the syringe needle as compared to an insertion pressure of a corresponding syringe needle in an article without the compliant portion; and
   wherein the compliant portion comprises a filled portion comprising a gel, a foam, or a combination comprising at least one of the foregoing.

2. The article of claim 1, wherein the syringe needle is a straight syringe needle; and
   wherein the filled portion is located in the casing tube at the casing tube end; and wherein the straight syringe needle traverses through the filled portion; or wherein the filled portion comprises a channel and the straight needle is located at a channel end located at the casing tube end; and/or
   wherein the filled portion is located in a tube portion located at the distal tube end.

3. The article of claim 1, wherein the filled portion has a modulus of 1 kilopascal to 10 megapascal.

4. The article of claim 1, further comprising a stabilizer comprising a stabilizer opening, wherein one or both of the syringe needle and a needle hub are located on a distal end of the syringe needle that traverses the stabilizer opening.

5. The article of claim 1, wherein the casing tube comprises a ridge at the distal tube end.

6. The article of claim 1, further comprising:
   a syringe located in the inner tube space of the casing tube; and
   a plunger located in an inner syringe space of the syringe;
   wherein the syringe comprises a syringe hub located at a hub barrel end of the syringe and a distal barrel opening located at a distal syringe end of the syringe; wherein the syringe hub is connected to the syringe needle.

7. The article of claim 6, wherein the syringe needle comprises a needle hub, wherein the needle hub is threadably engaged with the syringe hub or wherein the needle hub and the syringe hub are locked together via a locking mechanism.

8. The article of claim 6, wherein the syringe needle comprises a needle hub, and wherein the syringe hub is a slip tip located in the needle hub.

9. A compliant article comprising:
   a casing tube comprising a tube end opening located at a needle tube end of the casing tube, a distal tube opening located at a distal tube end of the casing tube, and an inner tube space; and
   a syringe needle that traverses the tube end opening;
   wherein the compliant article comprises a compliant portion that allows for a reduced insertion pressure of the syringe needle as compared to an insertion pressure of a corresponding syringe needle in an article without the compliant portion;
   wherein the compliant portion comprises a helical portion of the syringe needle; and wherein the syringe needle comprises the helical portion located in between a needle tip portion and a distal portion.

10. The syringe needle of claim 9, further comprising a needle hub located on the distal portion.

11. The syringe needle of claim 9, wherein the helical portion comprises 1 to 200 helical loops.

12. The syringe needle of claim 9, wherein the needle tip portion has one or both of an outer diameter of 1.7 to 0.1 mm and an inner diameter of 1.3 to 0.005 mm.

13. A compliant article comprising:
    a casing tube comprising a tube end opening located at a needle tube end of the casing tube, a distal tube opening located at a distal tube end of the casing tube, an inner tube space, a plunger located in the inner tube space, and a syringe needle that traverses the tube end opening;

wherein the compliant article comprises a compliant portion that allows for a reduced insertion pressure of the syringe needle as compared to an insertion pressure of a corresponding syringe needle in an article without the compliant portion.

14. The article of claim 13, wherein the syringe needle is a straight syringe needle, and wherein the compliant portion comprises a spring located in the casing tube, helically surrounding the straight needle.

15. The article of claim 13, wherein the compliant portion comprises a spring located in a spring tube portion located at the distal tube end of the casing tube.

16. A method of ejecting or taking in a fluid using a compliant syringe system comprising:
   inserting a syringe needle into a patient; and
   applying a pressure to the fluid and ejecting the fluid located in an inner tube space through the syringe needle; or withdrawing the fluid from the patient into the inner tube space through the syringe needle;
   wherein the compliant syringe system comprises a casing tube comprising a tube end opening located at a needle tube end of the casing tube, a distal tube opening located at a distal tube end of the casing tube, and the inner tube space; wherein the syringe needle traverses the tube end opening; wherein the syringe needle is located on a syringe that comprises the inner syringe space, a syringe hub located at a hub barrel end of the syringe, and wherein the syringe is located in the inner tube space of the casing tube;
   wherein the compliant syringe system comprises a compliant portion that allows for a reduced insertion pressure of the syringe needle as compared to an insertion pressure of a corresponding syringe needle in a syringe system without the compliant portion.

17. The method of claim 16, further comprising determining a stiffness of the patient's epidermis and selecting a stiffness of the compliant syringe system that is less than or equal to the stiffness of the patient's epidermis prior to the inserting.

\* \* \* \* \*